United States Patent
Stanley

(10) Patent No.: US 9,943,971 B2
(45) Date of Patent: Apr. 17, 2018

(54) CUTTING TOOL

(71) Applicant: Anthony G. Stanley, North Bay Village, FL (US)

(72) Inventor: Anthony G. Stanley, North Bay Village, FL (US)

(*) Notice: Subject to any disclaimer, the term of this patent is extended or adjusted under 35 U.S.C. 154(b) by 185 days.

(21) Appl. No.: 14/825,306

(22) Filed: Aug. 13, 2015

(65) Prior Publication Data

US 2016/0059427 A1    Mar. 3, 2016

Related U.S. Application Data

(60) Provisional application No. 62/044,555, filed on Sep. 2, 2014.

(51) Int. Cl.
| | | |
|---|---|---|
| *B26B 11/00* | (2006.01) | |
| *B26B 29/00* | (2006.01) | |
| *B26B 27/00* | (2006.01) | |
| *B26B 17/00* | (2006.01) | |
| *A61B 17/50* | (2006.01) | |
| *A61B 17/88* | (2006.01) | |

(52) U.S. Cl.
CPC .............. *B26B 17/00* (2013.01); *A61B 17/50* (2013.01); *A61B 17/8863* (2013.01)

(58) Field of Classification Search
CPC ........ A61B 17/50; A61B 17/8863; B26B 7/00
USPC ......................................................... 30/124
See application file for complete search history.

(56) References Cited

U.S. PATENT DOCUMENTS

| | | | | |
|---|---|---|---|---|
| 2,012,648 | A | * | 8/1935 | Wheeler ................ A01G 3/02 30/134 |
| 2,281,189 | A | * | 4/1942 | Wright ................ A01G 3/053 30/132 |
| 3,842,500 | A | * | 10/1974 | Cassel .................... B26B 17/00 30/124 |
| 4,464,837 | A | * | 8/1984 | Amstutz .............. A01G 3/0475 30/134 |
| D313,334 | S | * | 1/1991 | Novak ............................. D8/5 |
| 5,033,195 | A | | 7/1991 | Appelkvist et al. |
| 5,301,431 | A | * | 4/1994 | Cera .................. A61B 17/8863 30/186 |
| 5,365,625 | A | | 11/1994 | Han |
| 5,383,274 | A | | 1/1995 | Miller |
| 5,619,892 | A | * | 4/1997 | Eggert ..................... B25B 7/00 24/11 R |

(Continued)

OTHER PUBLICATIONS

Stanley, Dr. Anthony G.; International Patent Application No. PCT/US15/44976; International Search Report; dated Nov. 23, 2015; 2 pages.

(Continued)

*Primary Examiner* — Ghassem Alie
*Assistant Examiner* — Bharat C Patel
(74) *Attorney, Agent, or Firm* — Dority & Manning, PA

(57) ABSTRACT

A cutting tool is described. The cutting tool can provide increased safety in residential, commercial, and/or medical applications. The cutting tool includes a container that can catch and/or hold material that is cut by use of the tool. This can prevent the cut material from flying indiscriminately away from the cutting tool at high velocity and can also prevent the cut material from falling to the floor/ground after cutting. The cutting tool can be sterilized for medical use, such as fish hook or jewelry removal.

25 Claims, 16 Drawing Sheets

(56) References Cited

U.S. PATENT DOCUMENTS

| | | | |
|---|---|---|---|
| 5,653,029 A * | 8/1997 | Shigenaka | A01G 3/053 30/132 |
| 5,659,958 A * | 8/1997 | Goings | A01G 3/053 30/124 |
| 6,324,712 B1 | 12/2001 | Elsener, Sr. | |
| 7,021,177 B2 * | 4/2006 | Lovemark | B25B 7/18 81/417 |
| 7,111,376 B2 | 9/2006 | Lombardi et al. | |
| 7,424,777 B2 * | 9/2008 | Namvar | A01G 3/0475 30/131 |
| 8,522,443 B2 | 9/2013 | Latronico et al. | |
| 2005/0022633 A1 * | 2/2005 | Rozo | B25B 27/28 81/418 |
| 2006/0236548 A1 | 10/2006 | Namvar | |
| 2007/0157473 A1 * | 7/2007 | Varnell | A01G 3/0251 30/194 |
| 2009/0078278 A1 | 3/2009 | Tran | |
| 2009/0149868 A1 | 6/2009 | Shelton et al. | |
| 2009/0241342 A1 | 10/2009 | Habib | |
| 2009/0293686 A1 | 12/2009 | Pfab | |

OTHER PUBLICATIONS

Aven website; http://www.aveninc.com/avens-complete-product-line/tools/pliers-and-cutters/accu-cut-premium-pliers-and-cutters/accu-cut-xl-oval-head-cutter-2#.U-IOImd3uM8 ; webpage printed Sep. 25, 2015; (4 pages).

Ted Pella, Inc website; http://www.tedpella.com/tools_html/cutters.htm#_oval ; webpage printed Sep. 25, 2015; (8 pages).

Stantley pliers #89-858 Fat Max—3 Photos. Printed Sep. 25, 2015; (3 pages).

Knipex diagonal cutters; http://www.zoro.com/knipex-diagonal-cutters-7-14-in-74-12-160/i/G6419585/ ; webpage printed Sep. 25, 2015; (2 pages).

Lindstrom; PDF catalogue; p. 31; printed Sep. 28, 2015; http://www.google.com/url?sa=t&rct=j&q=&esre=s&source=web&cd=8&ved=0CFAQFjAHahUKEwjmu7zAk5bHAhXEbD4KHSIOB4c&url=http%3A%2F%2Fwww.lindstromtools.com%2Fpdf_down.php&ei=djbEVeaoNMTZ-QGinJy4CA&usg=AFQjCNEngyRCOyvTghht1GbVWqEtR5BsGw&bvm=bv.99804247,d,cWw.

Swanstrom Tools USA; http://www.swanstromtools.com/choose.htm ; printed Sep. 14, 2015; (4 pages).

* cited by examiner

CUTTING TOOL

CROSS REFERENCE TO RELATED APPLICATION

This application claims filing benefit of U.S. Provisional Application Ser. No. 62/044,555 having a filing date of Sep. 2, 2014, which is incorporated herein by reference in its entirety.

BACKGROUND

The need often arises to cut materials of a relatively small cross section such as wires, nails, and so forth. Unfortunately, this need also arises quite often in the medical industry, as foreign objects must be removed from individuals either due to accidental impalement (e.g., embedded fish hooks, nails, wires, etc.) or due to infection at the site of intentionally embedded materials (e.g., jewelry). In both cases, common wire cutters are often used.

The use of a common hand tool in a medical application presents health and safety issues. For instance, time may be lost in treatment while the proper hand tool is located, often by contacting the environmental services department of the treatment facility. Sterility of the tool is also an issue, as quickly cleaning the tool as provided may not be enough to ensure proper hygienic conditions for the patient. Moreover, tools designed for construction and home repair use are not always of the best design for use in a medical application. For instance, removal of a barbed hook from a patient requires forcing the barb through and out of the skin at a point distal from the entrance point, cutting off of the barb on the end of the hook, and then pulling the remains of the hook back out of the patient. This requires dear visualization of the hook and desirably is carried out with a minimal amount of trauma to the patient. Wire cutters designed for home repair use often have thick and bulky jaws that impede visualization as well as handles that are difficult to dose with suitable force in the dose quarters of the medical procedure.

In all applications of the use of cutting tools, e.g., medical applications, home repair applications, construction applications, etc., the sudden release of the cut material can also be a problem. For instance, when cutting the barbed end off of a fish hook, the sudden release of the barb can cause the barb to fly through the air at a very high velocity. Similarly, when snipping the end off of a wire, nail, etc. at a construction site, the cut pieces can form high velocity projectiles that fly indiscriminately across the site. Such high velocity projectiles can be dangerous, particularly if they should happen to hit someone in the eye. Moreover, once these projectiles have landed, they can be difficult to find again, and may be stepped on, which can cause trauma to an unprotected foot and can cause floor damage if embedded in a shoe.

What are needed in the art are safer cutting tools. For instance, what are needed are cutting tools that contain or hold the material that is released upon cutting. Moreover, what are needed are cutting tools specifically designed for use in medical applications.

SUMMARY

According to one embodiment, disclosed is a cutting tool. More specifically, the cutting tool can include a first jaw piece, a second jaw piece, a joint, a first and second handle, and a container. Each of the two jaw pieces can include a cutting edge, a beveled surface, and an upper surface, with the beveled surface being between the cutting edge and the upper surface. The two jaw pieces can terminate at the joint, and the joint can have a closed position such that at the closed position the cutting edges meet one another. The handles can extend from the joint and control movement of the jaw pieces. The cutting tool also has a container that includes a first section and a second section that are attached to the jaw pieces. Specifically, the first section includes an attachment edge and a meeting edge, with this attachment edge being attached to the top surface of the first jaw piece. The second section also includes an attachment edge and a meeting edge, with this attachment edge being attached to the top surface of the second jaw piece. When the joint is in the closed position, the meeting edges of the two sections meet or overlap one another to form a closed container.

During use, the container can serve to catch and/or hold material that is snipped free at the cutting edge. This can prevent accidents and damage that can be caused by the high velocity release of materials when using the tools including damage from the material as it flies away from the cutting edge as well as damage from the material after it has landed, for instance foot trauma from stepping on pieces previously cut with the tool.

In one embodiment, the cutting tool can be a medical device. In this embodiment, the cutting tool can be formed of sterilizable materials and maintained in conjunction with other sterilized tools, for instance in an emergency room, trauma unit, private doctor's office, medical clinic (e.g., urgent care), etc.

The cutting tool can be utilized to safely remove objects that have been embedded in an individual such as fish hooks, nails, jewelry, etc. For instance, a method of utilizing a medical cutting tool can including cutting an end off of a foreign object that has been embedded in a person or animal by use of the mated cutting edges of a sterile cutting tool, catching or holding the end of the object within the container of the cutting tool, and then removing the remainder of the foreign object from the person or animal.

BRIEF DESCRIPTION OF THE FIGURES

A full and enabling disclosure of the present invention, including the best mode thereof, directed to one of ordinary skill in the art, is set forth in the specification, which makes reference to the appended figures, in which.

Figure 1:
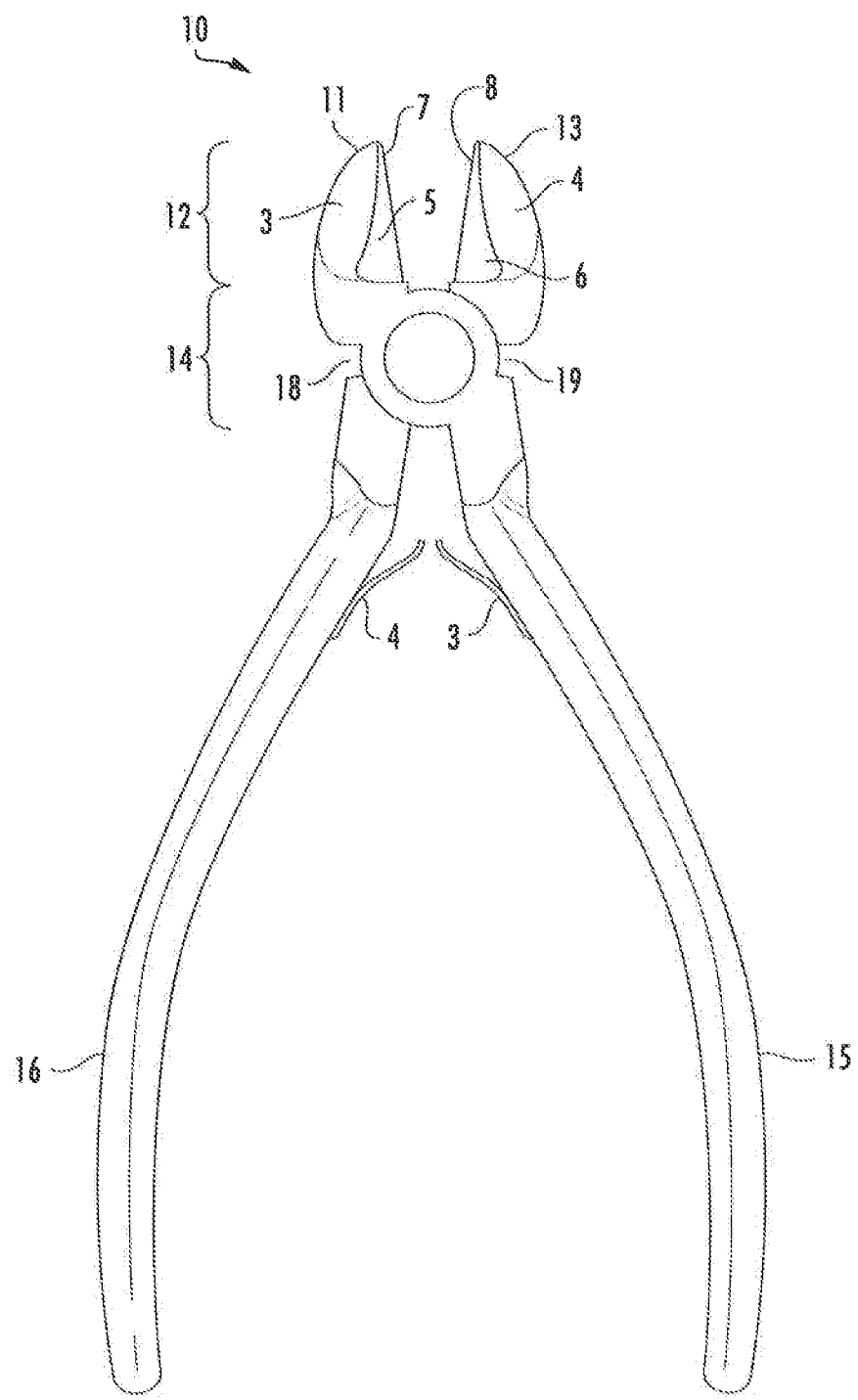
FIG. 1 is a front view of one embodiment of a cutting tool.

Repeat use of reference characters throughout the present specification and appended drawings is intended to represent same or analogous features or elements of the invention.

DETAILED DESCRIPTION

Reference now will be made in detail to embodiments of the disclosed subject matter, one or more examples of which are illustrated in the drawings. Each example is provided by way of explanation of the subject matter, not limitation thereof. In fact, it will be apparent to those skilled in the art that various modifications and variations can be made to the presently disclosed subject matter without departing from the scope or spirit of the disclosure. For instance, features illustrated or described as part of one embodiment can be used with another embodiment to yield a still further embodiment. Thus, it is intended that the present disclosure covers such modifications and variations as come within the scope of the appended claims and their equivalents.

The present disclosure is generally directed to a cutting tool that can provide increased safety in use including, for instance, residential, commercial, and/or medical applications. More specifically, the cutting tool includes a container that can catch and/or hold material that is cut by use of the tool. This can prevent the cut material from flying indiscriminately away from the cutting tool at high velocity and can also prevent the cut material from falling to the floor/ground after cutting. This not only makes clean-up easier, but prevents the fallen pieces from causing foot trauma or floor damage.

The cutting tool can include other features that can make it easier and safer to use, particularly in medical applications. For example, the cutting tool can have a lower profile, which can improve visualization when using near skin and thus decrease the chance of nicking the patient's skin. In addition, the cutting tool can include handles that are easy to grip and can have dual action spring loading. This can allow for medical personnel to more easily close the jaw of the tool with adequate force to successfully cut the targeted materials in a single action, thus causing less trauma to the patient.

Referring to FIG. 1, one embodiment of a cutting tool 10 is illustrated. The cutting tool generally includes a jaw 12 that in turn includes a first jaw piece 11 and a second jaw piece 13. The cutting tool 10 also includes a joint 14, a first handle 15 and a second handle 16.

Each jaw piece 11, 13 includes a cutting edge 7, 8, respectively. As shown in FIG. 1, the jaw is in an open configuration and as such the cutting edges 7, 8 are separated. The cutting edges can be formed of a hardened material that can hold an edge over a long period of time and can cleanly cut a metal. For example, the cutting edges 7, 8 can be formed of a hardened steel, such as a high-grade alloy steel or carbon steel including, without limitation, M2 high-speed carbon steel, W2 carbon tool steel, O1 alloy tool steel, CPM-M4 steel, D2 high chromium content tool steel, S30V stainless steel, 154CM stainless steel, ZDP-189 stainless steel, etc. The cutting edges can have a hardness on the Rockwell Hardness C scale of from about HRC 55 to about HRC 65, or from about HRC 60 to about HRC 65, or from about HRC 63 to about HRC 65 in some embodiments.

In one embodiment, at least the jaw 12 and joint 14 sections of the cutting tool 10 can be formed of the material used to form the cutting edges. For instance, the cutting tool 10 can be formed of a first unitary piece that forms handle 16, a portion of the joint 14 and jaw piece 13 and a second unitary piece that forms handle 15, a portion of the joint 14 and jaw piece 11 and these two unitary pieces can be held together in a rotating relationship at joint 14, for instance with an interlocking screw and nut or the like. Other materials, such as cushioning covers for the handles, can also be employed. Alternatively, the handles can be formed of a separate material, though a joining of different materials can affect the overall strength of the cutting tool. In one embodiment, the cutting tool can include disposable handle covers, which can provide for ease in sterilization with improved comfort during use.

When considering the cutting tool for medical applications, all materials used to form the cutting tool can be sterilizable. Thus, the cutting tool can be sterilized and maintained for medical use, for instance as a component of a trauma kit, in a medical setting such as an emergency room, trauma unit, private doctor's office, medical clinic (e.g., urgent care facility), etc.

The cutting edges 7, 8 can have any suitable edge shape including, without limitation, a semi-flush edge with a slight bevel, a flush edge with a minimum bevel, or a no bevel edge, as are generally known in the art. In one embodiment, the cutting edges can have a no bevel edge and can produce a cut with no pinch on the edge of the cut material. This edge shape may decrease the applied force necessary to produce the cut, which may prove beneficial when considering use in a medical application in which the person handling the tool may be more likely to have small hands as compared to, for instance, a construction application. However a hand tool having a no bevel cutting edge may also have a reduced cutting life as compared to other cutting edges.

The jaw 12 of the cutting tool 10 also includes beveled surfaces 5, 6 that extend up from the cutting edges 7, 8 respectively. The beveled surfaces 5, 6 connect to upper surfaces 3, 4 of the jaw.

The joint 14 of the cutting tool 10 can be a standard joint as is generally known in the art and include, for instance an interlocking screw and nut mounted on bearing rings. The joint can include various features such as friction reducing O-rings and the like that can improve cutting action. The joint can include stops 18, 19 that can define the widest possible open position of the cutting tool 10. For instance, in the embodiment of FIG. 1, the cutting tool 10 is in an open position, but is not at the farthest open position at which point the stops 18, 19 would close and restrict any further opening between the cutting edges 7, 8.

The handles 15, 16 can be of a length to ensure adequate leverage by a user at the cutting edges 7, 8 of the cutting tool 10. For instance, the handles 15, 16 can generally be from about 3 inches to about 8 inches in length, or from about 4 inches to about 5.5 inches in some embodiments. The length of the handles 15, 16 can ensure that a user can firmly grip the cutting tool 10 across the width of their hand, thus spreading the pressure across the entire hand width and preventing a point force on the palm. Suitable length of the handles 15, 16 can also allow a user to engage all four fingers during use and increase compressive force at the cutting edges 7, 8. The handles 15, 16 can also include a padded surface and one or more devices to improve grip, as discussed further herein.

The cutting tool can also have dual action provided by one or more springs located between the handles. Dual action ensures that following a cut the jaw will open by merely releasing pressure on the handles. Particularly when utilizing the cutting tool near a person's skin surface, it is beneficial to have a tool that will automatically open at the cutting edges 7, 8 without the need for actively spreading the jaw open. The dual action capability, e.g., by addition of the presence of one or more springs, can also reduce the hand fatigue of the operator.

In the embodiment of FIG. 1, the dual action is provided by a pair of leaf springs 33, 34 that are attached to the handles 15, 16 respectively and meet between the handles when the cutting tool 10 is closed (i.e., when the cutting edges 7, 8 meet). Any suitable spring action device can be utilized, and it should be understood that the cutting tool is not limited to the utilization of mated leaf springs as illustrated in FIG. 1. For instance, a single leaf spring can be utilized or alternatively one or more coiled springs can be utilized. The spring action device need not be exceptionally strong, particularly as an excessively strong spring action device will increase the compressive force needed to cut a material at the cutting edges 7, 8. The spring action device need only be strong enough to force the joint 14 to an open position upon release of pressure at the handles.

Figure 2:
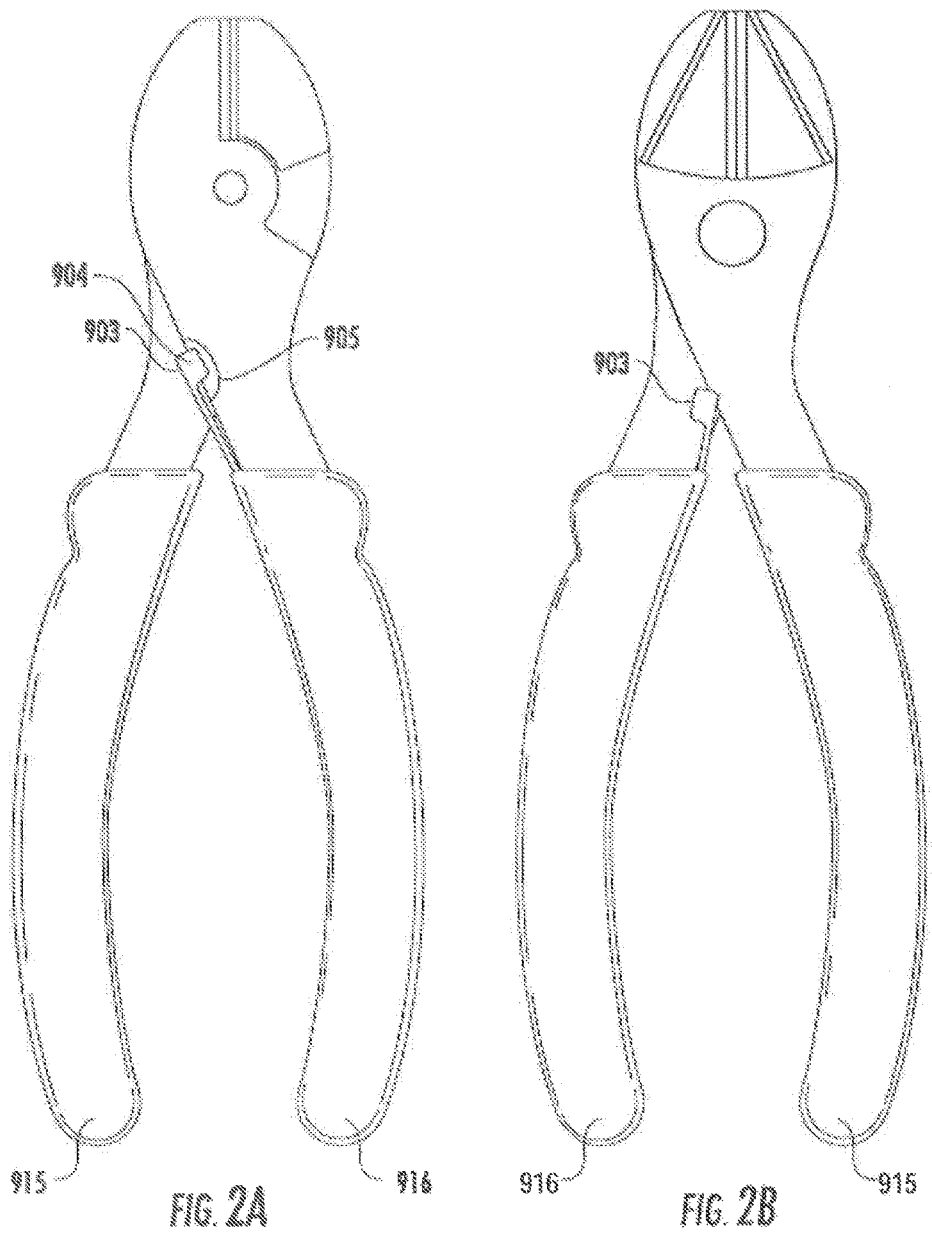
FIG. 2A illustrates a back view of a cutting tool including a spring loading pin in the inoperative position.
FIG. 2B illustrates a front view of a cutting tool including a spring loading pin in an operative position.

In one embodiment, the cutting tool can include an optional spring action. One example of this embodiment is illustrated in FIG. 2A and FIG. 2B. According to this embodiment, the cutting tool can include a leaf spring 903 that can be located in either an inoperable mode (FIG. 2A) or in an operable mode (FIG. 2B). In the inoperable mode, the leaf spring 903 can be attached to one of the handles 916 in such a fashion that it does not contact the other handle. For instance, in the illustrated embodiment, the leaf spring 903 can be secured to the handle 916 and the handle 916 can include an inset 905 into which the head 904 of the leaf spring 903 can fit. By locating the head 904 of the leaf spring 903 in the inset 905 during the inoperable mode, the leaf spring can be securely held under no bending pressure.

In order to utilize the cutting tool in the spring action mode, the head 904 of the leaf spring 903 can be slid out of the inset 905 and moved over to contact the handle 915 as shown in the front view of FIG. 2B. In this orientation, the leaf spring can contact the second handle 915 as shown. The angle of the leaf spring 903 can be such that when the handles 915, 916 are in the closed position, the leaf spring 903 can exert a force on the handle 915 to push the handles apart and open the jaws of the cutting tool. Though illustrated as a generally rectangular head 904, it should be understood that the head 904 of the leaf spring 903 can be of any desired shape including, without limitation, flat, hooked, semi-circular, circular, etc.

Figure 3:
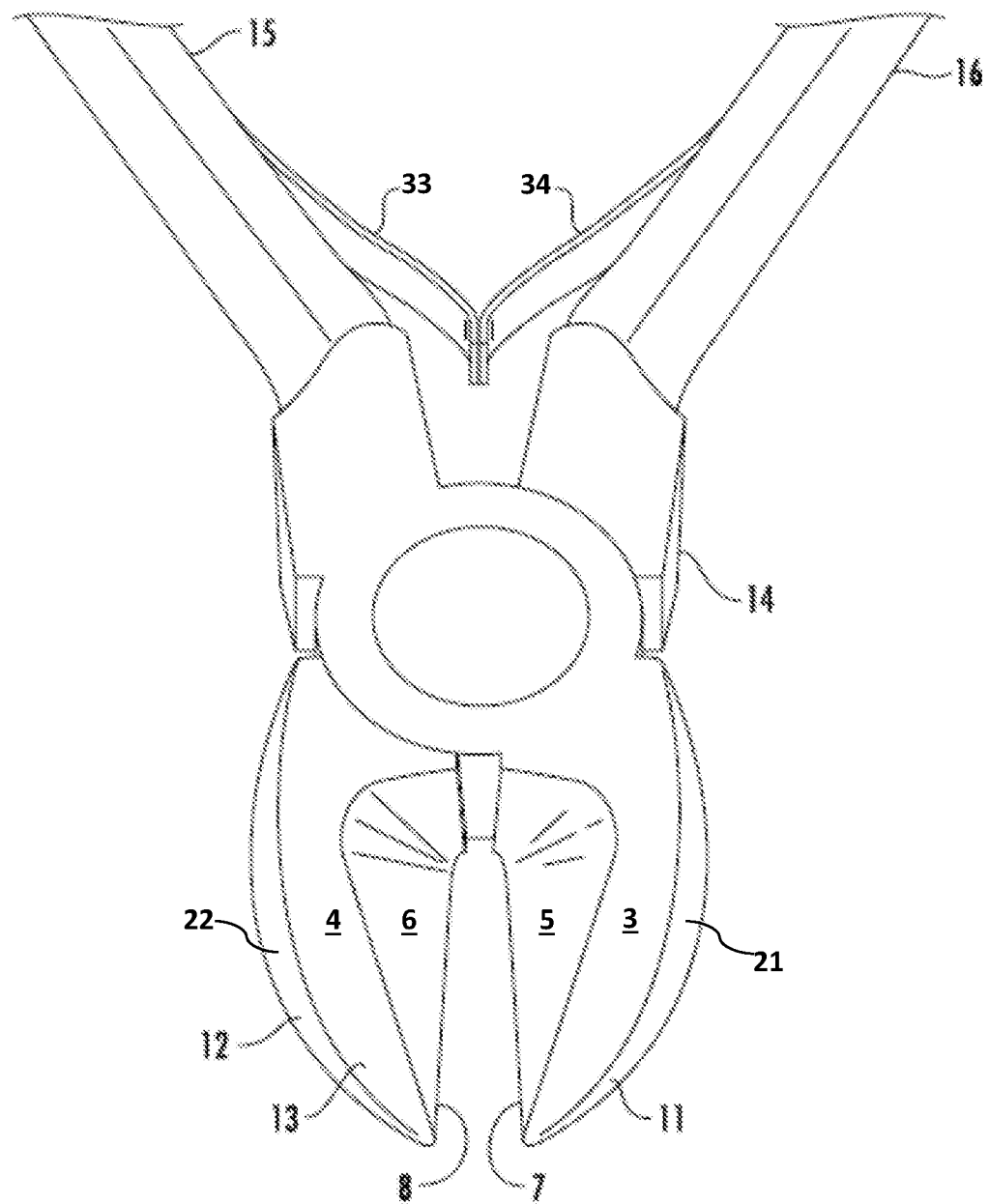
FIG. 3 is a perspective view of the cutting tool of FIG. 1.

FIG. 3 is a end perspective view of the cutting tool 10 and illustrates the jaw 12, the joint 14 and the upper end of the handles 15, 16 including the leaf springs 33, 34. As shown in this image, the leaf springs will encounter one another between the two handles 15, 16 before the cutting edges 7, 8 meet. As such, the leaf springs will be under tension when the joint 14 is in the closed position and the cutting edges 7, 8 meet, and upon release of the pressure the leaf springs 33, 34 will open the jaw pieces 11, 13.

Figure 4:
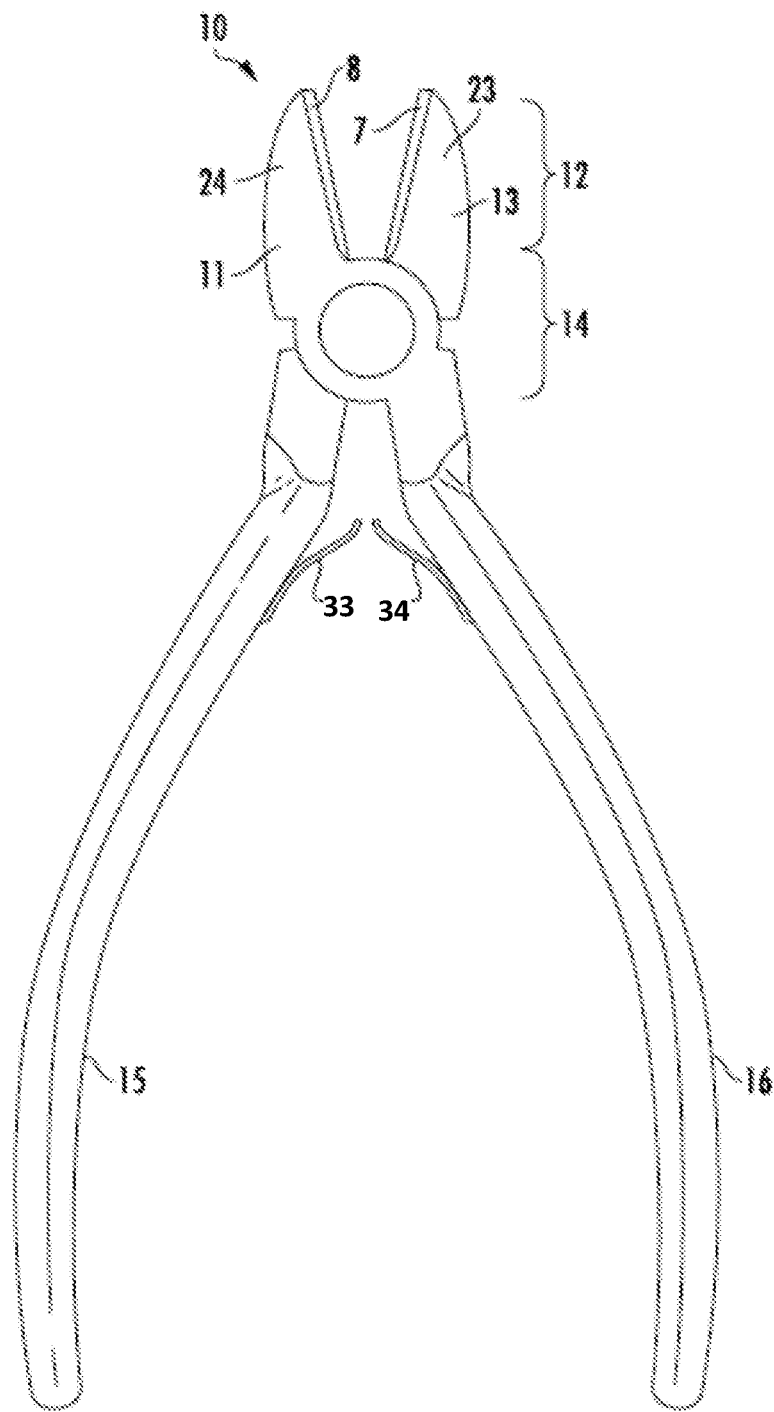
FIG. 4 is a back view of the cutting tool of FIG. 1.

FIG. 4 is a back view of the cutting tool 10 illustrated in FIG. 1. FIG. 4 illustrates the back view of the jaw 12, the joint 14, and the handles 15, 16, as discussed above. As shown, the leaf springs 33, 34 extend from the handles 15, 16 to meet in between the handles when the joint 14 is in a closed position. Cutting edge 7 is adjacent to lower surface 23 of jaw piece 13 and cutting edge 8 is adjacent to lower surface 24 of jaw piece 11 as shown.

Figure 5:
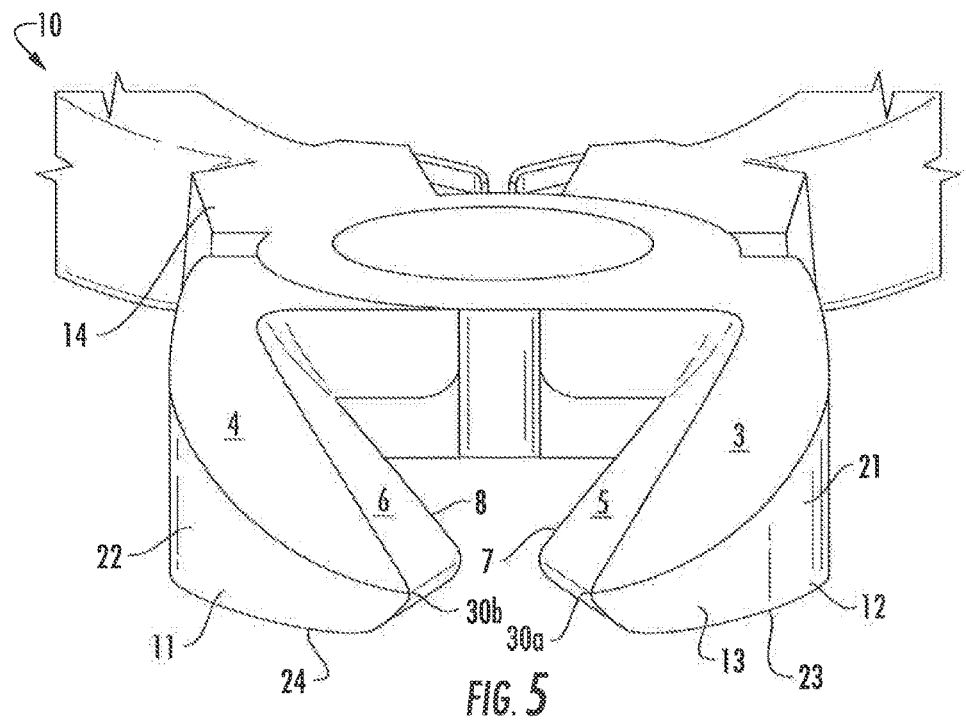
FIG. 5 is another view of the cutting tool of FIG. 1.
Figure 6:
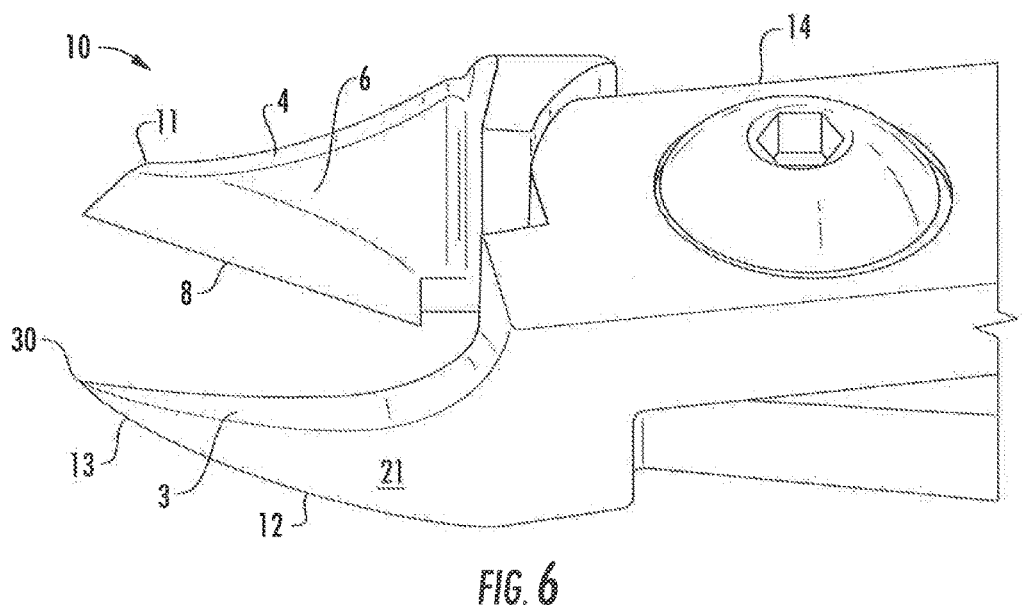
FIG. 6 is a side view of the cutting tool of FIG. 1.

FIG. 5 is an end view and FIG. 6 is a side view of the cutting tool 10, and more specifically of the jaw 12 and joint 14 sections of the cutting tool 10. The beveled surface 5 is between the cutting edge 7 and the upper surface 3 of jaw piece 13 and the beveled surface 6 is between the cutting edge 8 and the upper surface 4 of jaw piece 11. The upper surface 3 extends from the beveled surface 5 to the outer side surface 21 of jaw piece 13 and the upper surface 4 extends from the beveled surface 6 to the outer side surface 22 of jaw piece 11.

In one embodiment, the geometry of the jaw pieces of the cutting tool can be designed for beneficial use in a medical application for use with either humans or animals. For example, the jaw pieces can have a lower profile than is common for a typical hand tool so as to provide improved visualization for use of the tool near the skin of a patient. For instance the height of the outer side surfaces 21, 22, of a jaw piece 13, 11 respectively can be lower than that for a typical hand tool, to provide improved visualization. As shown, the outer side surface 21 extends from the lower surface 23 to the upper surface 3 of the jaw piece 13 and the outer side surface 22 extends from the lower surface 24 to the upper surface 4 of the jaw piece 11.

The height of the outer side surface can vary from the tip of the jaw 30 to the termination of the jaw at the joint 14, as shown. In one embodiment, and with reference to FIG. 9A, 9B, 9C, the maximum height of the outer side surface can be at the termination of the jaw piece where the jaw piece 82 meets the joint 84. This is not a requirement, however, and the maximum height of the outer side surface can be prior to the termination of the jaw piece in some embodiments. This maximum height for the outer side surface can be, for example, between about 5 millimeters and about 10 millimeters, or from about 6 millimeters to about 8 millimeters in one embodiment.

Referring again to FIG. 5 and FIG. 6, in this embodiment the upper surfaces 3, 4, can be concave from the tip of the jaw 30 to the termination of the jaw at the joint 14, with a radius of curvature extending toward the lower surfaces 23, 24 and the arc of this curvature extending from the tip of the jaw 30 toward the joint 14 of the jaw as shown in FIG. 6. Thus, in this embodiment, the height of the side surfaces 21, 22 can be somewhat lower than typical hand tool cutters to improve visualization.

In order to maintain the overall strength of the jaw in those embodiments in which the side surfaces of the jaw pieces are designed with lower profiles for improved visualization, the width of the jaw pieces can be increased. For instance, the width of the upper surface 3 from the beveled surface 5 to the outer side surface 21 and the width of the upper surface 4 from the beveled surface 6 to the outer side surface 22 can be wider than that of a typical hand cutting tool. The particular width of the jaw piece can vary depending upon the materials used to form the tool, the height of the outer side surfaces, the length of the jaw, the desired strength of the cutting tool with regard to cutting force at the cutting edges, and so forth.

As shown in FIG. 5, the upper surface 3 and the upper surface 4 can also exhibit some outward curvature away from the cutting edges 7, 8 along the length of the jaw 12 from the tip 30a, 30b of the jaw pieces 13, 11 toward the termination of the jaw pieces 13, 11 at the joint 14. This can increase the width of the upper surfaces 3, 4 along these lengths and further increase the strength of the jaw 12 and the cutting tool 10.

Figure 7:
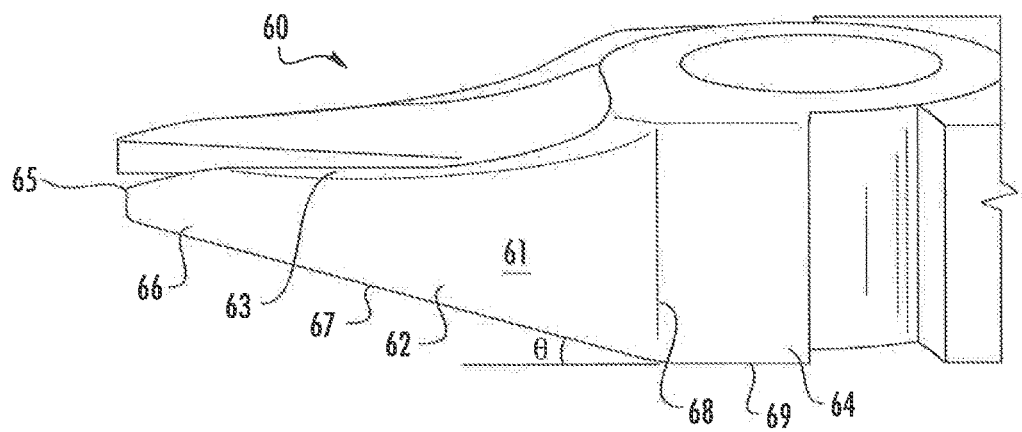
FIG. 7 is a side view of one embodiment of a cutting tool

FIG. 7 is a side view of another embodiment of a jaw 62 and a portion of a joint 64 of a cutting tool 60. As can be seen in this embodiment, the outer side surface 61 meets the upper surface 63 at a line that exhibits some curvature from the tip 65 of the jaw piece 66 toward the termination of the jaw piece 66 at the joint 64. The radius of this curvature is toward the lower surface 67 of the jaw piece thus lowering the profile of the jaw piece and improving visibility during use, particularly in medical applications. A line of demarcation 68 can be seen at the termination of the jaw piece 66 and the initiation of the joint 64 of the tool cutter 60. This line is not a requirement, but in this embodiment illustrates a general demarcation between the jaw and the joint of a device.

Also at the junction between the jaw 62 and the joint 64, the lower surface 67 of the jaw piece 66 can meet the lower surface 69 of the joint 64 at an angle. For instance, the angle θ between the lower surface 67 of the jaw piece 66 and the extension of a line along the lower surface 69 of the joint 64 in the direction of the jaw (equivalent to, e.g., a surface such as a table top upon which the cutting tool 60 can sit when resting on the lower surface 69 of the joint 64) can be from about 10° to about 30°, from about 12° to about 20° or about 16° in some embodiments.

Figure 8:
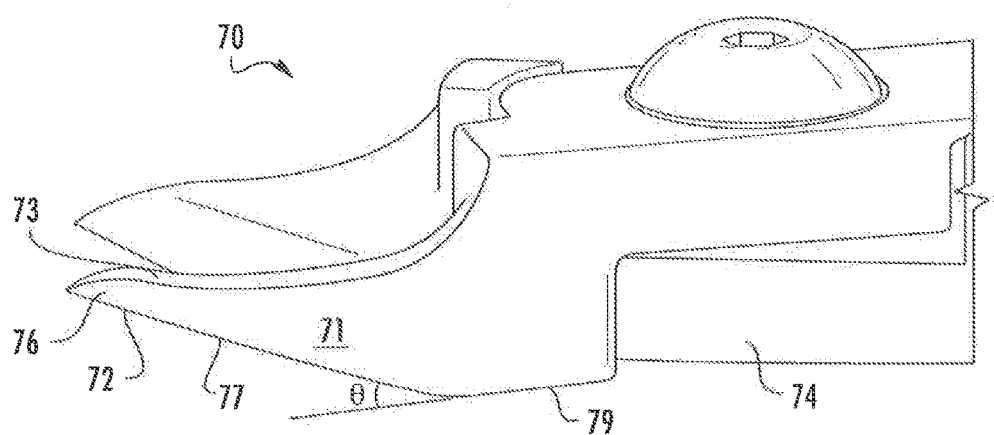
FIG. 8 is a side view of one embodiment of a cutting tool

FIG. 8 illustrates the jaw 72 and joint 74 of another embodiment of a cutting tool 70. This particular embodiment includes a different profile line as compared to the embodiments of FIG. 1 and FIG. 7. Similar to these embodiments, however, the line at which the outer side surface 71 meets the upper surface 73 can describe a curvature having a radius toward the lower surface 77 of the jaw piece 76. This provides a very low profile tool with excellent visibility for close work.

The angle θ between the lower surface 77 of the jaw piece 76 and the extension of the lower surface 79 of the joint 74 in the direction of the jaw (e.g., along the table top) can be as described above, e.g., from about 10° to about 30°, from about 12° to about 20° or about 16° in some embodiments.

Figure 9A:
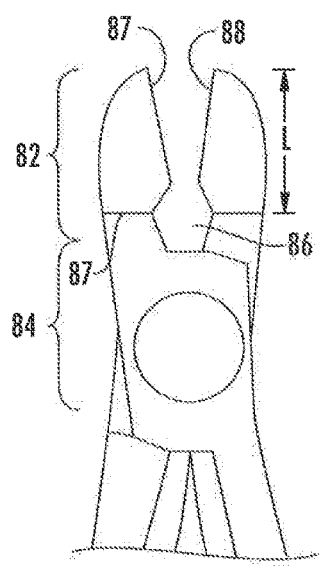
FIG. 9A is a front view of one embodiment of a cutting tool.
Figure 9B:
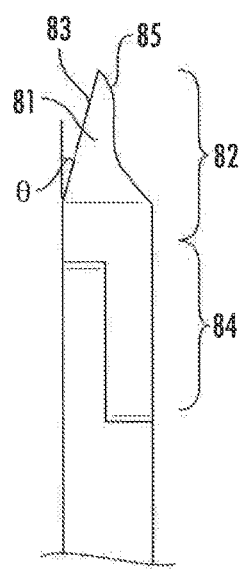
FIG. 9B is a side view of one embodiment of a cutting tool
Figure 9C:
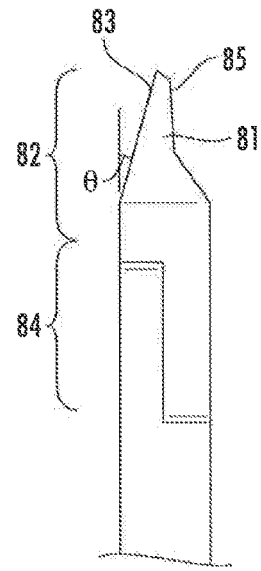
FIG. 9C is a side view of one embodiment of a cutting tool.

FIG. 9A, FIG. 9B, and FIG. 9C illustrate a front view (FIG. 9A) and side views (FIG. 9B, FIG. 9C) of embodiments of a cutting tool. Referring to FIG. 9A, the jaw 82 of a cutting tool can generally have a length 'L' from the tip 88 of the jaw 82 to the termination 87 of the jaw 82 where the jaw 82 meets the joint 84 of from about 7 millimeters to about 15 millimeters, for instance from about 8 millimeters to about 13 millimeters or from about 9 millimeters to about 12 millimeters in some embodiments.

FIG. 9B and FIG. 9C illustrate two different profile shapes as may be utilized for the jaw 82. As shown, the profile of jaw 82 of the cutting tool of FIG. 9B is somewhat more rounded at the upper edge of the outer side surface 81 as compared to that of the outer side surface 81 of the cutting tool of FIG. 9C. In both cases, however, the profile is relatively low between the lower surface 83 and the upper surface 85 of the jaw piece of the cutting tools, which can improve visibility. As discussed above, the angle 74 can be between about 10° to about 30°.

As illustrated in FIG. 9A, the tool can include a wider section 86 that is distal to the cutting edges 87, 88. This section 86 can be used to grasp a relatively large piece of material.

In general, the cutting tool can be sized to cut material having a cross sectional dimension equivalent that of about 12 gauge wire or less, for instance about 14 gauge wire or less, or about 16 gauge wire or less in some embodiments. Thus, the cutting tool can be utilized to quickly and efficiently cut electrical wires sized for about 30 amps or less, such as about 20 amps or less as well as non-electrical wires, nails, tacks, fish hooks, body jewelry, etc.

When considering medical applications including both human and animal applications, the cutting tool can be sized to cut materials that are commonly embedded in individuals such as fish hooks, dental wires, surgical wires etc. as well as jewelry such as belly button rings, nose rings, barbells (e.g., ear, nose tongue, nipple, etc.), and the like that may need to be removed due to infection or other purposes. The cutting tool can also be utilized for hygiene applications such as nail clipping for either animals or humans.

Figure 10:
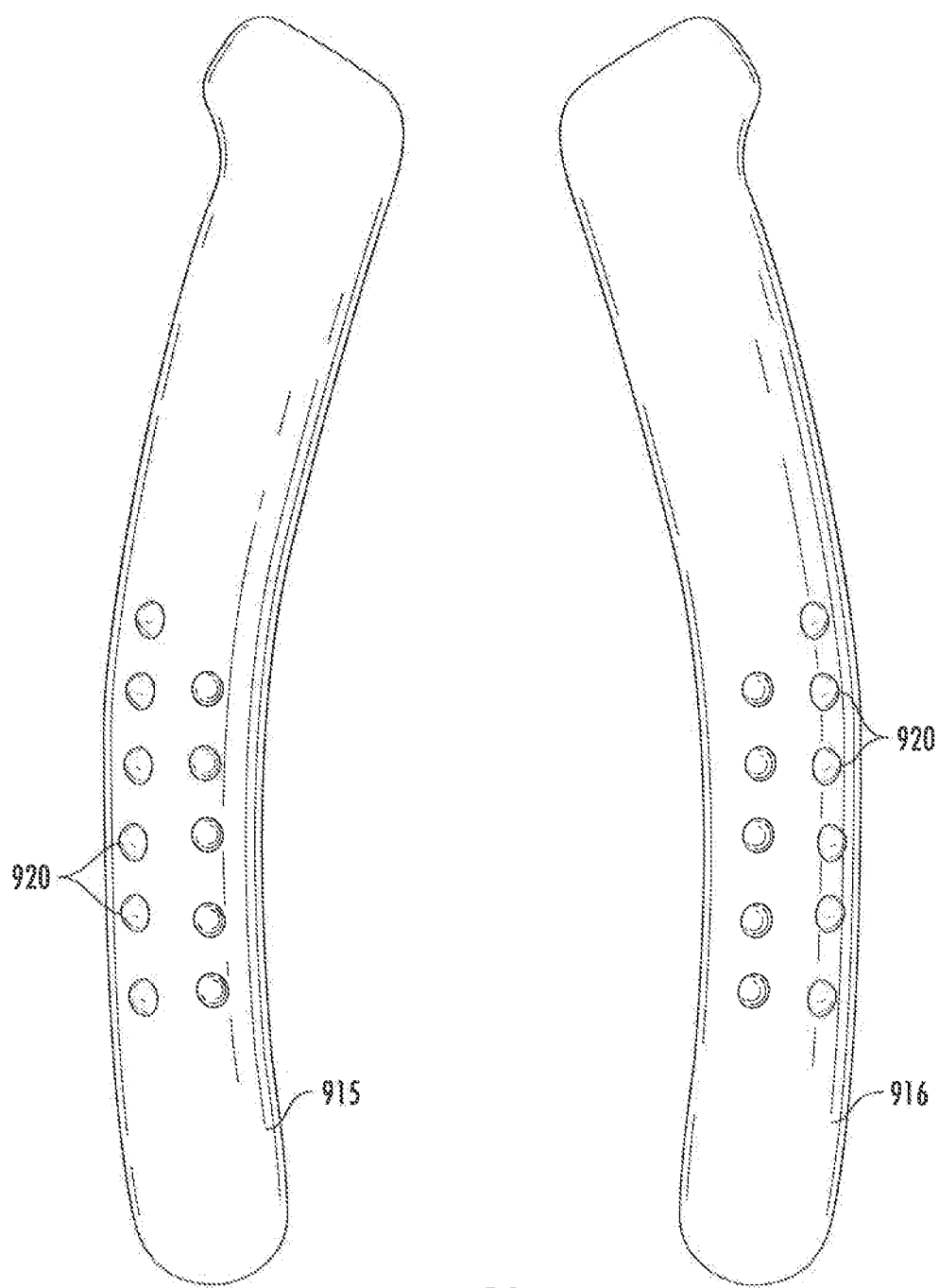
FIG. 10 illustrates left and right handle covers of a cutting tool.

As mentioned, the cutting tool can include handle components that improve grip and the ability to apply suitable compressive force at the cutting edges so as to quickly and efficiently cut a material even when being used by someone with relatively small hands. Examples of possible components are illustrated in FIG. 10 including handle covers 915, 916 and gripping projections 920.

The handle covers 915, 916 can be formed of a soft, deformable material such as an elastomeric foam or other relatively soft elastomer that provides for easy and stable gripping of the handles. For instance, the handle covers 915, 916 can be formed of a natural or synthetic rubber or silicone elastomer that can optionally be in the form of a foam. The handle covers 915, 916 can generally be adhered to the surface of a metal handle so as to prevent slipping during use. For instance, the handle can be unitary with the joint and jaw of a cutting tool and the handle covers can be adhered to the handle by use of, e.g., an adhesive or a melt bond. Alternatively, the handle covers 915, 916 can be simply held by a friction fit to the inner metal handle.

The handle covers 915, 916 can include a non-slip surface due to the nature of the material used to form the handle covers 915, 916. For instance, a latex or synthetic rubber composition can be molded to form the handle covers and upon formation can naturally include a somewhat rough surface to provide a non-slip grip to the handle covers.

Additional components can be utilized to further improve the grip of the handles. For instance, and as illustrated in FIG. 10, the handle covers 915, 916 can also include a series of gripping projections 920 on the surface of the handle covers. The gripping projections 920 can extend slightly from the surface of the handle covers 915, 916 to improve grip and the non-slip characteristic of the handles.

The gripping projections 920 can be circular as illustrated in FIG. 10. This is not a requirement of the gripping projections, however, and in other embodiments the gripping projections can have a non-circular cross section including an ovoid, square, triangular, rectangular, or other shape as well as a linear shape that can run circumferentially, axially, helically, or in any other direction or combination of directions along the surface of the handles or handle covers.

The gripping projections 920 can be applied to the surface of the handles in pattern or randomly. For instance, a series of gripping projections 920 can be applied in a pattern or randomly in the general area at which contact between the palm and/or the fingers of a user will grasp the handles or handle covers. The density of the gripping projections over the surface of the handle or handle covers can also vary, generally depending upon the expected contact areas between the hand of a user and the handles. By way of example, the handles can include a high density of gripping projections in those areas at which the palm and/or fingers are expected to contact the handles, and few or no gripping projections in other areas of the handles or handle covers.

The gripping projections 920 can be formed of the same material as handle covers or a different material. For instance, in one embodiment the gripping projections can be formed of a polymeric material that is somewhat harder than the material forming the handle covers. Exemplary polymeric materials can include, for example, a polyurethane material, a polyolefin material (e.g., a polyethylene or a polybutylene), a polyvinyl chloride, or the like. In this embodiment, the gripping projections can be adhered to the handle covers by use of an adhesive or can be melt bonded to the handle covers. Alternatively the gripping projections can be formed of the same material as the handle covers and formed simultaneously with the handle covers as a projecting extension of the handle covers.

Figure 11:
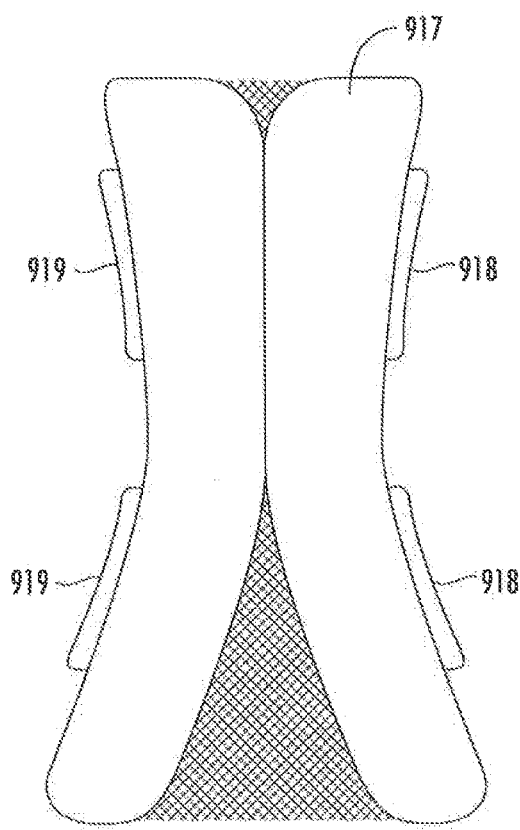
FIG. 11 illustrates a handle cover for use with a cutting tool.

In one embodiment, the cutting tool can include disposable handle covers that can be attached to a handle for use and then later removed. This can be of beneficial use in those embodiments in which a higher degree of sterility is desired, e.g., medical applications. FIG. 11 illustrates one embodiment of a disposable handle cover 917. As shown, the handle cover 917 can have a suitable shape and size for wrapping around and covering the handle of a cutting tool. A disposable handle cover 917 can be formed of an elastomeric foam or other relatively soft elastomer as discussed above.

The handle cover 917 can include a series of components 918, 919 for locking the handle cover on the handle. For instance, the components 918, 919 can include a series of tabs and notches in which the tabs can be pressed and temporarily locked into the notches. For removal of the handle covers from a handle following use, the tabs can be pulled out of the notches.

Figure 12:
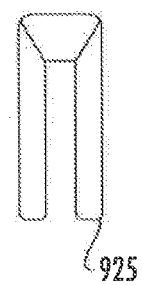
FIG. 12 illustrates a clip that can be used to lock a handle cover in place.
Figure 13:
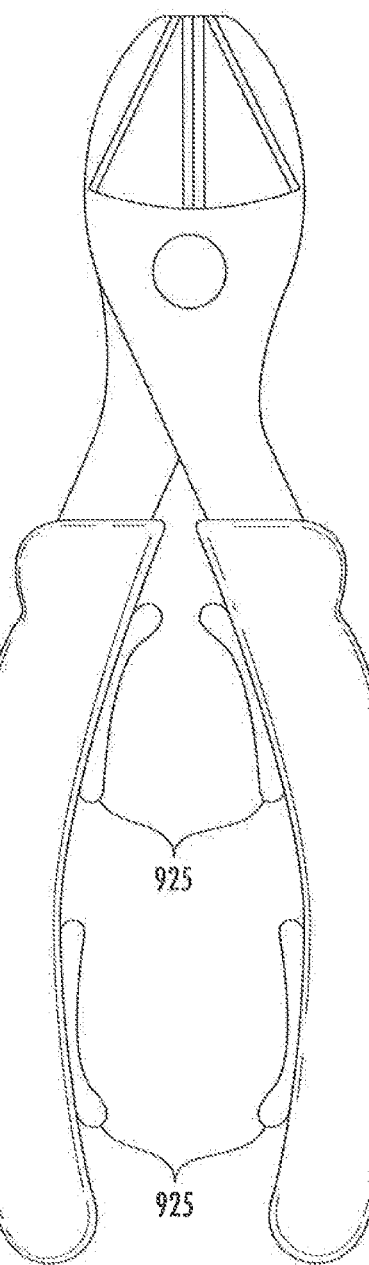
FIG. 13 illustrates a cutting tool including replaceable handle covers locked over the handles.

In one embodiment, a sliding lock 925 as illustrated in FIG. 12 can be used to lock the handle covers on the handles. In this embodiment, upon wrapping a handle cover 917 around the handle of a cutting tool as illustrated in FIG. 13, the components 918, 919 can meet one another. A sliding lock 925 can then be slid over the two components 918, 919, for instance along a groove in one of the components 918, 919 to hold the components 918, 919 together. To remove the handle covers 917 following use, the sliding lock 925 can be simply slid back off of the components 918, 919 and the handle covers 917 can be removed from the cutting tool.

Figure 14:
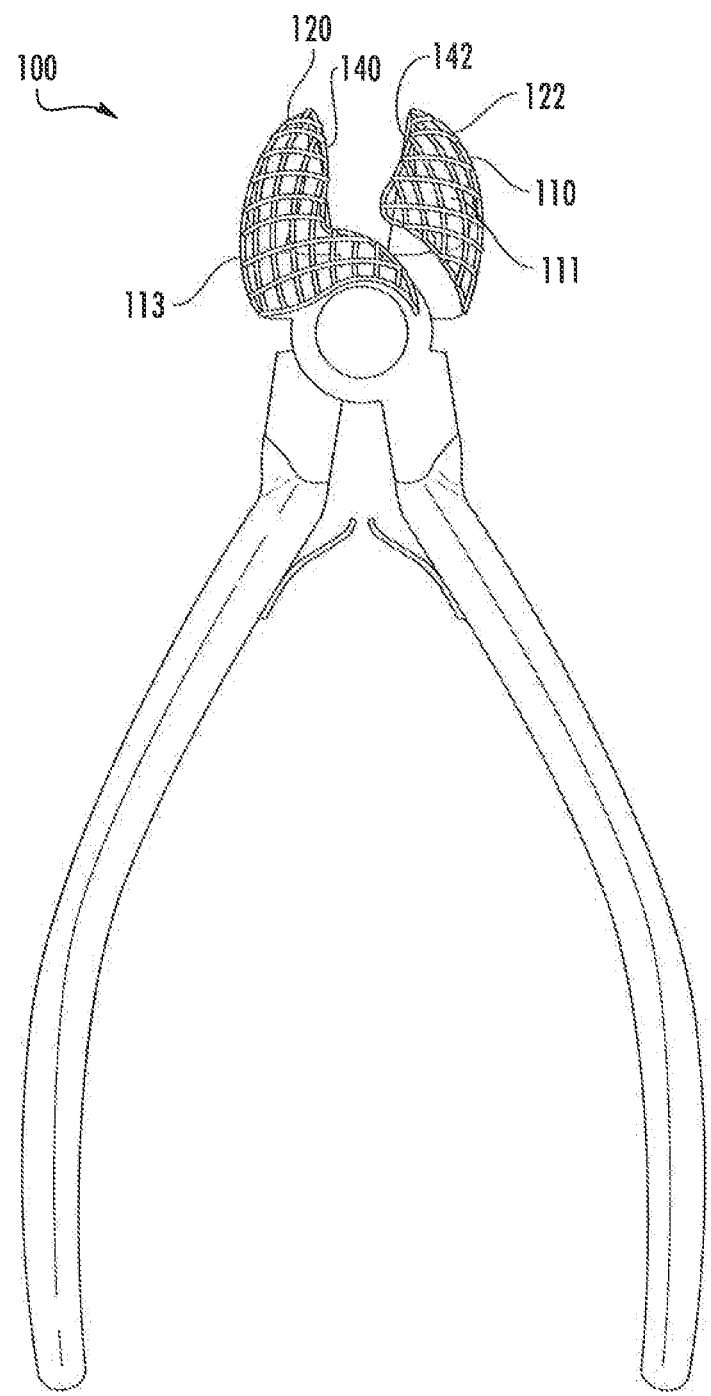
FIG. 14 is a front view of one embodiment of a cutting tool including a container.
Figure 15:
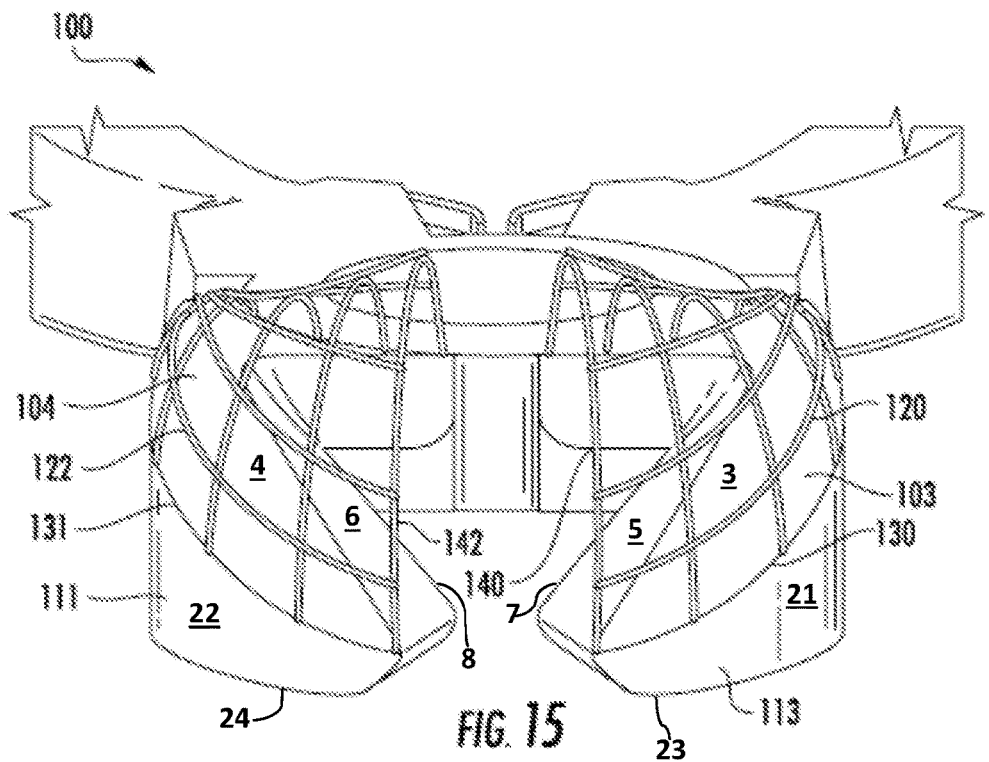
FIG. 15 illustrates a front end view of a cutting tool including a container.

As mentioned previously, the cutting tool can also include a container that can serve to catch and/or hold material that is cut by the tool. FIG. 14 illustrates a cutting tool 100 that includes such a container. As can be seen, the container 110 includes a first section 120 and a second section 122. The first section 120 is attached to the first jaw piece 113 and the second section 122 is attached to the second jaw piece 111. More specifically, the first and second sections 120, 122 of the container 110 are attached to the first and second jaw pieces 113, 111 at an attachment edge that is at or near the top surface of the jaw piece. This may be more clearly seen in FIG. 15 and FIG. 16, which are a front end view and a side view respectively, of a cutting tool 100.

The attachment edge 130 of the section 120 adheres to the top surface 103 of the jaw piece 113 and the attachment edge 131 adheres to the top surface 104 of the jaw piece 111. From the attachment edges 130, 131, the first and second sections 120, 122 of the container 110 rise above the top surfaces 103, 104 of the jaw pieces 113, 111. The first and second sections 120, 122 can be adhered to a surface of the jaw (generally the top surfaces of the jaw pieces, but this is not a requirement) according to any suitable fashion including, without limitation, use of an adhesive, melt bonding, welding, etc. Moreover, the attachment edge can be a continuous line or can be formed from a series of attachment points, such as a series of the termini of mesh components that form a container. In addition, the container sections can be permanently affixed to the jaw pieces or can be removable. For instance, the container can be added to the jaw of the cutting tool for use those circumstances in which it may be helpful for the particular cutting application, and may be removed for applications in which it is not deemed necessary. The container sections can also be replaceable with other sections of a different size or material.

The first and second sections 120, 122 of the container 110 also have meeting edges 140, 142. When the cutting tool is used, and the joint 114 is in the closed position, the meeting edges 140, 142 of the container will meet to form a closed container that extends up and over the top surfaces 103, 104 of the jaw pieces 113, 111. The meeting edges 140, 142 can either meet flush with one another upon the closing of the jaw or alternatively, may overlap somewhat along all or a portion of the length of the meeting edges. Thus, when material is snipped free by use of the cutting edges of the jaw, this loose material can be held within the container 110 and prevented from being projected out and through the air.

The container 110 can be formed of a material that can stop flying projectiles freed at the cutting edge and can also not impede visualization of the cutting edges. For instance, the container sections can be formed of a mesh, such as a metal or polymeric mesh that has openings large enough to allow visualization but small enough to catch a relatively small projectile. By way of example, the openings can be about 1 millimeter or less, about 0.75 millimeters or less or about 0.5 millimeters or less in cross section.

Figure 16:
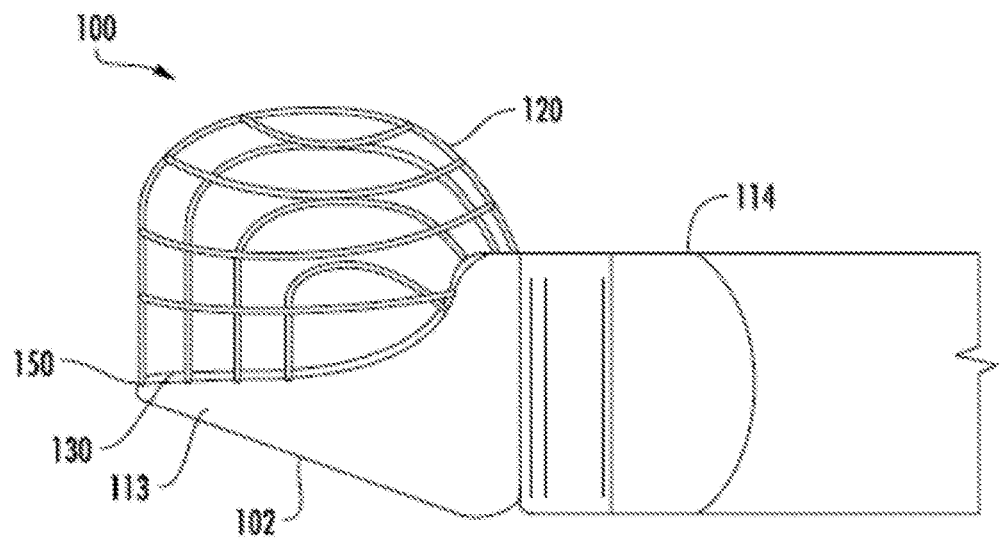
FIG. 16 illustrates a side view of a cutting tool including a container.

The profile of the container is not particularly limited, but as illustrated in FIG. 16, can generally rise to a maximum from the tip 150 of the jaw 102 and extend to roughly the area where the jaw 102 meets the joint 114. The overall shape and size of the container can be varied, however, provided that it covers the general area over the cutting edges so as to stop projectiles released at the cutting edge.

The profile of the container and the jaw can be designed to provide a particular ornamental 'look' to the cutting tool. For instance, as illustrated in FIG. 16, one embodiment of the cutting tool can have a profile similar to the classical shape of a sperm whale. Other ornamental and design choices are encompassed herein.

Figure 17:
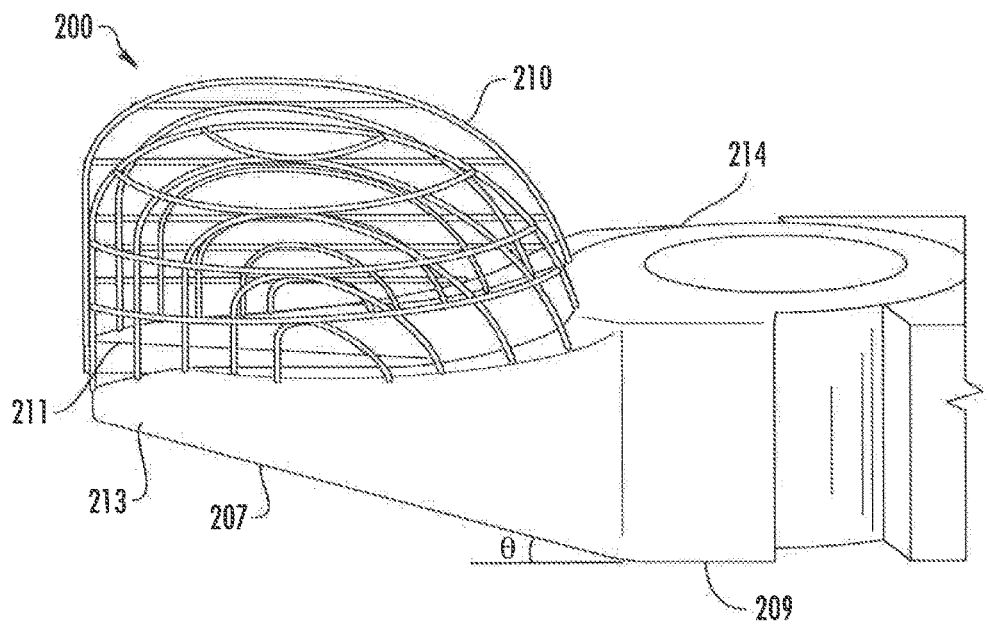
FIG. 17 illustrates a side view of one embodiment of a cutting tool including a container.
Figure 18:
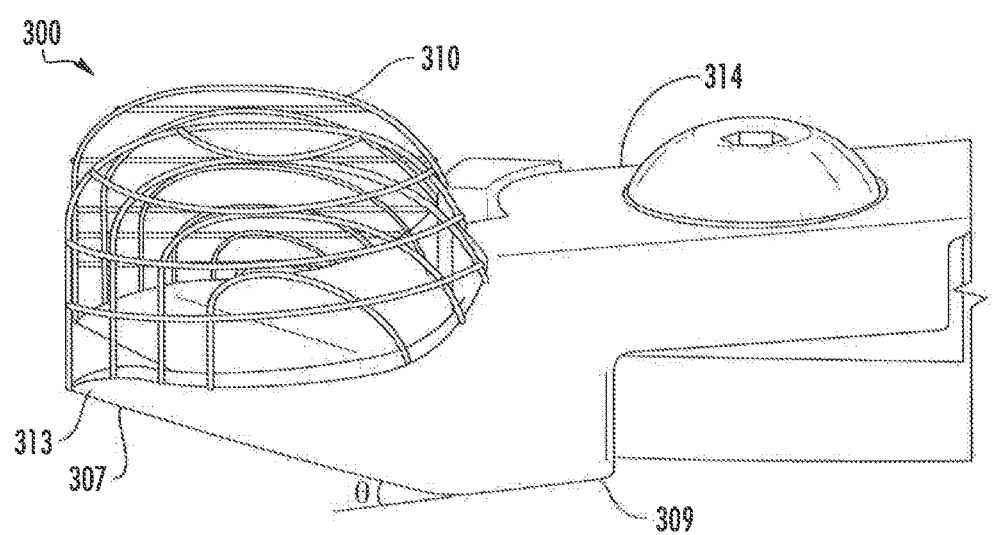
FIG. 18 illustrates a side view of one embodiment of a cutting tool including a container.

FIG. 17 is a side view of another cutting tool 200 including a container 210 that extends up and over the jaw pieces 211, 213. FIG. 18 is a side view of another cutting tool 300 including a container 310 as described. As discussed above, the cutting tools can have an angle θ between the bottom surface 207, 307 of the jaw piece 213, 313 and the line extension of the bottom surface 209, 309 of the joint 214, 314 of the cutting tool 200, 300 in the direction of the jaw.

Figure 19A:
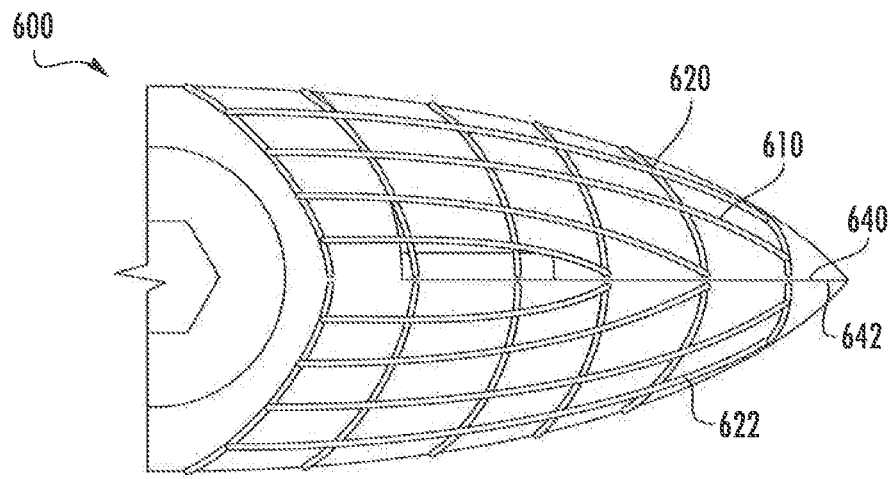
FIG. 19A and 19B illustrate one embodiment of a cutting tool including a view in a closed orientation (FIG. 15A) and a view in an open orientation (FIG. 19B).
Figure 19B:
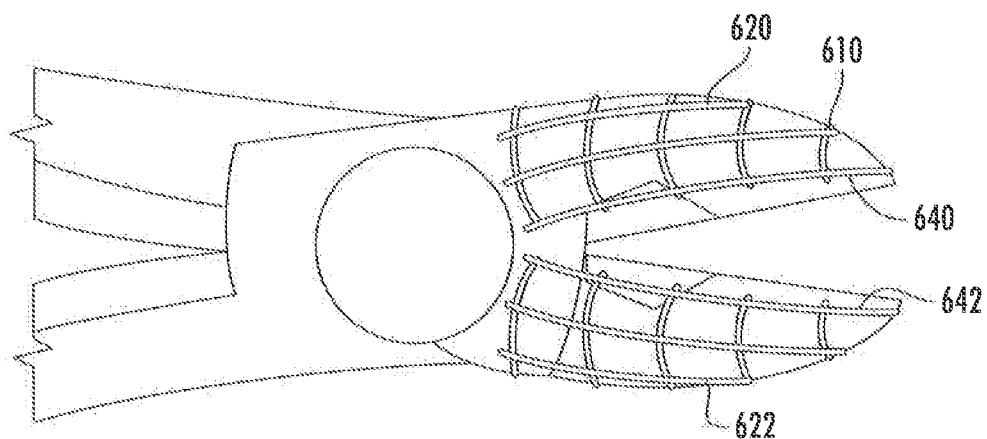

FIG. 19A and 19B present views of a cutting tool 600 in a closed (FIG. 19A) and open (FIG. 19B) configuration. This clearly illustrates the meeting edges 640, 642 of the first section 620 and the second section 622 of the container 610. In the closed configuration (FIG. 19A), the meeting edges 640, 642 meet to close the container 610 and prevent loss of material cut by the tool. In the open configuration (FIG. 19B), the meeting edges 640, 642 open with the jaw of the cutting tool 600.

Figure 20A:
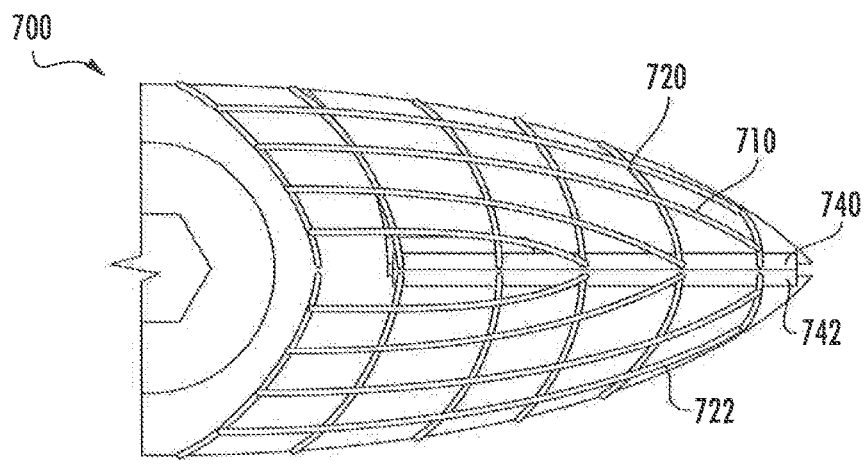
FIG. 20A and 20B illustrate one embodiment of a cutting tool including a view in a closed orientation (FIG. 20A) and a view in an open orientation (FIG. 20B).
Figure 20B:
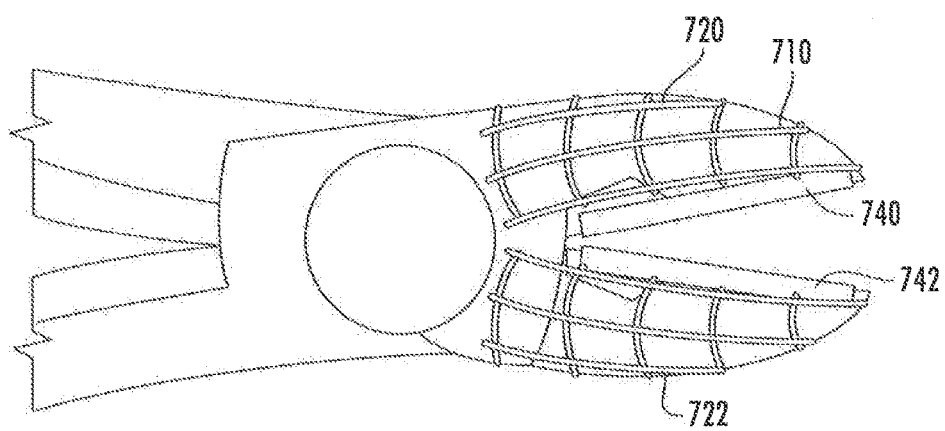

The container can be formed of a single material or can be a composite of several materials. For instance, in FIG. 20A and FIG. 20B is illustrated a cutting tool 700 including a container 710 formed of a first section 720 and a second section 722. The bulk of the container 700 is formed of a mesh that can stop flying projectiles while still allowing visualization of the cutting edges of the cutting tool 700, as discussed.

The meeting edge 740 includes at the edge a deformable material such as a rubber or other elastomeric material. The meeting edge 742 likewise includes at the edge a deformable material such as a rubber or other elastomeric material. This deformable material can allow for the container upon closing to firmly grasp and hold a material. For instance, when cutting a material that has a length that extends from the cutting edges and beyond the height of the container, such as a longer wire, nail, or the like, it can prove beneficial to grasp the material by use of the meeting edges 740, 742 as the material is cut. Upon cutting, the now loose piece is held between the meeting edges 740, 742 by the deformable material, and the user can avoid dropping the loose piece to the floor or ground. The deformable material can extend along the entire length of the meeting edges 740, 742 or only along a portion of the length, as desired. In addition, though illustrated as including a deformable material on both meeting edges 740, 742, in other embodiments, a cutting tool may include a deformable material on only one of the two meeting edges, which can still improve the grasping capability of a container at the meeting edges.

Figure 21:
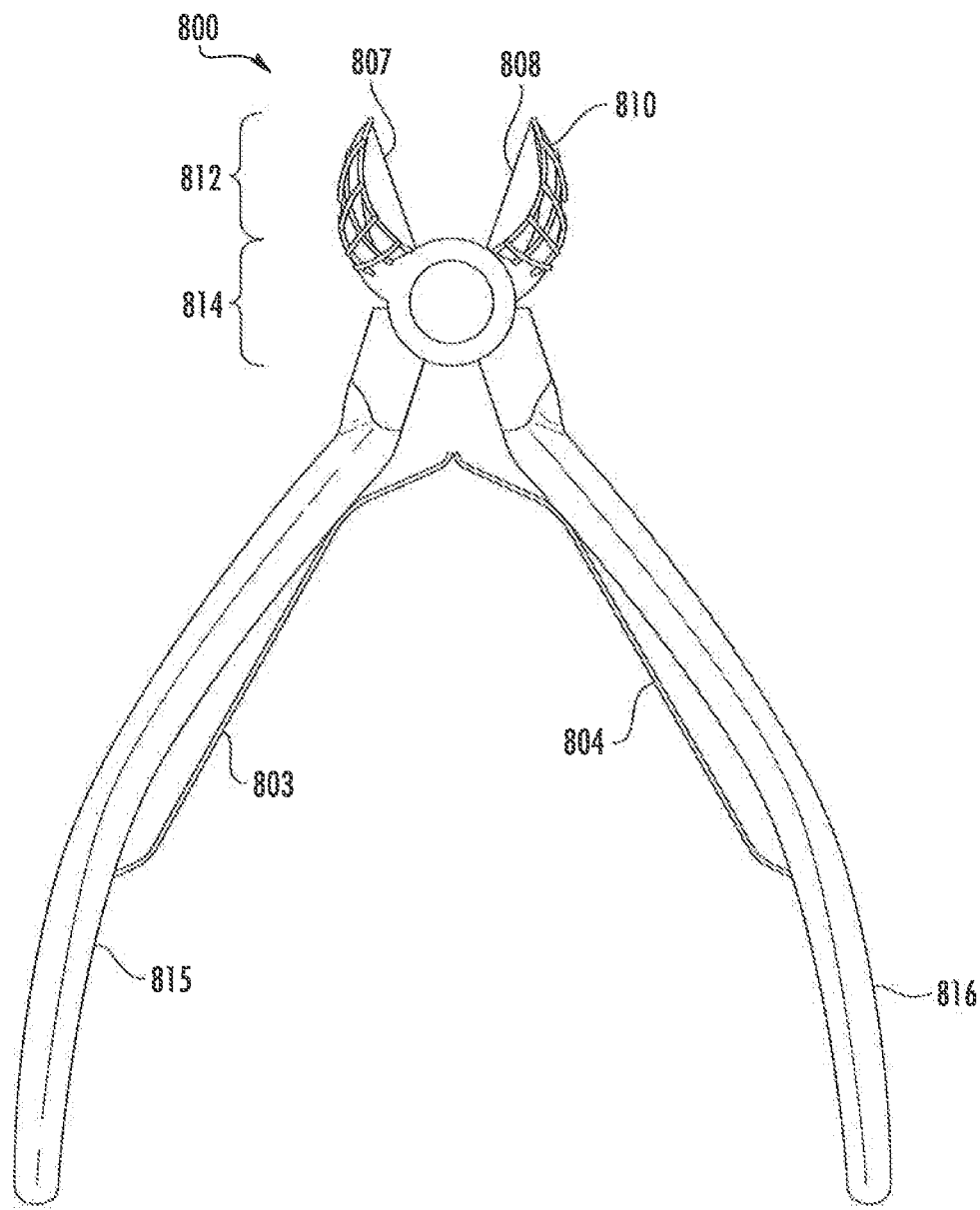
FIG. 21 illustrates a front view of one embodiment of a cutting tool including a container.

FIG. 21 illustrates another embodiment of a cutting tool 800 including a container 810 for catching and/or holding materials cut at the cutting edges 807, 808 of the jaw 812 of the tool 800. The jaw 812 is controlled via the joint 814 by the handles 815, 816. The cutting tool 800 has dual action handles as provided by the matching leaf springs 803, 804 located between the handles 815, 816.

Figure 22:
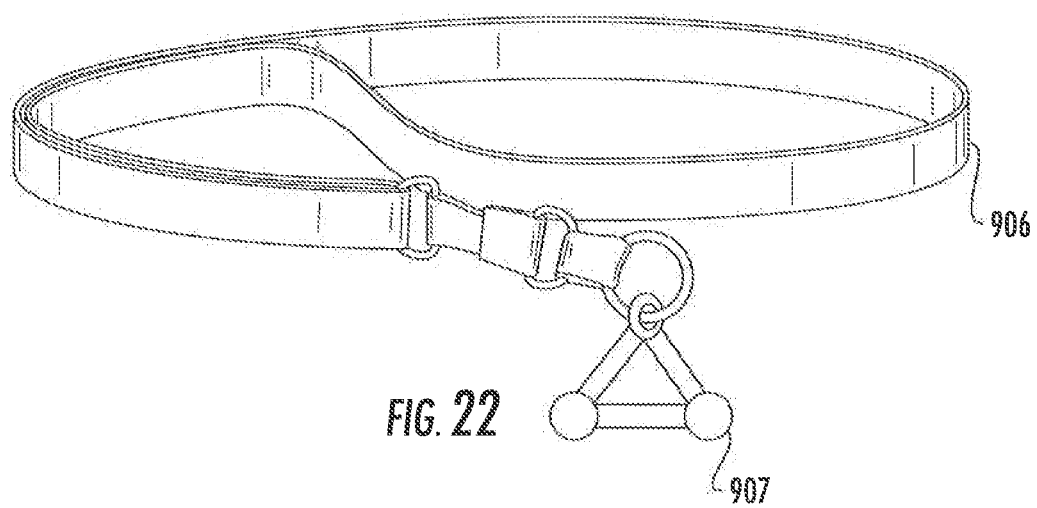
FIG. 22 illustrates a hanging loop attached to a lanyard for use in storing a cutting tool.
Figure 23:
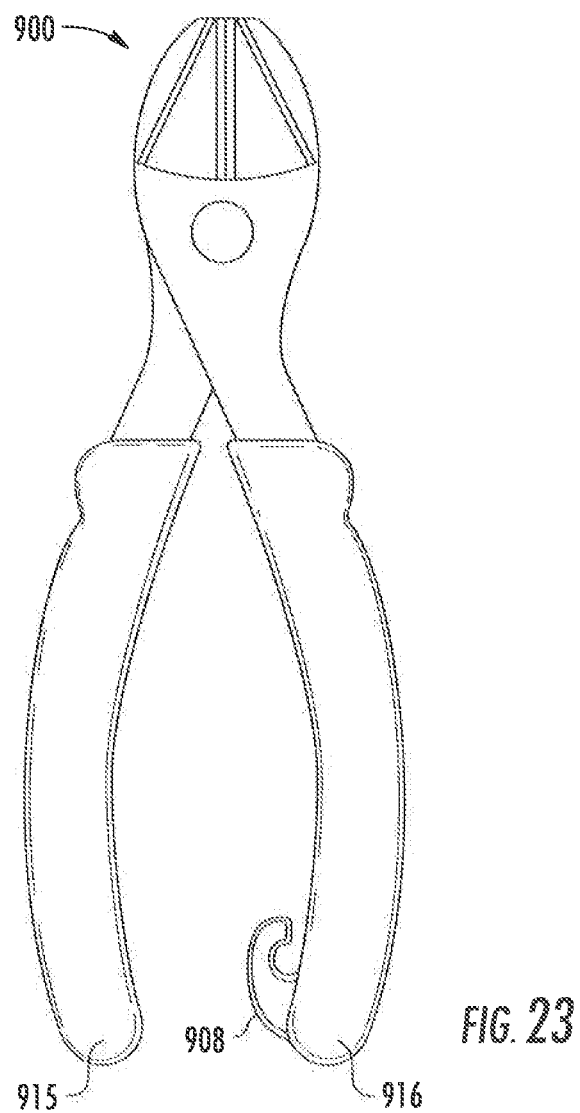
FIG. 23 illustrates a cutting tool including a hook for hanging the tool for storage.

A cutting tool can include a storage mechanism. For example, as illustrated in FIG. 22 and FIG. 23, a cutting tool 900 can include a hook 908 (FIG. 23) by which the cutting tool can be hung for storage. In one embodiment, the cutting tool can also include a loop 907 specifically designed for use with the hook 908. For instance, the loop 97 can be held on a lanyard 906 and the cutting tool 900 can be suspended by use of the hook 908 and loop 907. This can free up use of the hands during use while keeping the device nearby and preventing dropping of the cutting tool 900 during use. In general, the hook 908 and loop 907 can be molded from plastic or metal, and the hook 908 can be affixed to the handle 916 via an adhesive, melt bonding, or the like.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A cutting tool comprising:
   a first jaw piece, the first jaw piece including a first cutting edge, a first beveled surface, a first upper surface, a first outer side surface and a first lower surface, the first beveled surface being between the first cutting edge and the first upper surface, the first outer side surface being between the first upper surface and the first lower surface and the first lower surface being between the first outer side surface and the first cutting edge;
   a second jaw piece, the second jaw piece including a second cutting edge, a second beveled surface, a second upper surface, a second outer side surface and a second lower surface, the second beveled surface being between the second cutting edge and the second upper surface, the second outer side surface being between the second upper surface and the second lower surface and the second lower surface being between the second outer side surface and the second cutting edge;
   a joint, the first jaw piece and the second jaw piece terminating at the joint, the joint having a closed position, the first and second cutting edges meeting one another with no portion of the first and second upper surfaces overlaying one another with the joint at the closed position;
   a first handle extending from the joint;
   a second handle extending from the joint;
   a container comprising a first section and a second section, the first section including a first meeting edge, the first section being attached to the first jaw piece such that the first section is in contact with one or more of the first upper surface, the first outer side surface, and a first boundary where the first upper surface meets the first outer side surface, the first boundary and the first meeting edge being spaced apart from one another in both a vertical distance as measured above the first upper surface and in a horizontal distance as measured across the first upper surface, the second section including a second meeting edge, the second section being attached to the second jaw piece such that the second section is in contact with one or more of the second upper surface, the second outer side surface, and a second boundary where the second upper surface meets the second outer side surface, the second boundary and the second meeting edge being spaced apart from one another in both a vertical distance as measured above the second upper surface and in a horizontal distance as measured across the second upper surface, the first meeting edge and the second meeting edge contacting one another with the joint at the closed position and thereby defining a container volume having a height that extends above the first and second upper surfaces and having a width that extends along a line between the first boundary and the second boundary.

2. The cutting tool of claim 1, wherein the cutting edges are formed of a hardened carbon steel or a hardened alloy steel.

3. The cutting tool of claim 1, wherein the first jaw piece, a first portion of the joint, and the first handle are portions of a first unitary piece and the second jaw piece, a second portion of the joint, and the second handle are portion of a second unitary piece.

4. The cutting tool of claim 1, wherein all materials of the cutting tool are sterilizable.

5. The cutting tool of claim 1, wherein the cutting tool comprises one or more springs.

6. The cutting tool of claim 5, wherein the one or more springs are one or more leaf springs.

7. The cutting tool of claim 5, wherein the one or more springs are movable to an operable and an inoperable location on the cutting tool.

8. The cutting tool of claim 1, wherein the first upper surface defines a radius of curvature that extends toward the first lower surface and wherein the second upper surface defines a radius of curvature that extends toward the second lower surface.

9. The cutting tool of claim 1, wherein the joint includes a lower joint surface, an angle between the first lower surface and a line extending from the lower joint surface in the direction of the jaw being from about 10° to about 30°.

10. The cutting tool of claim 1, further comprising a first handle cover and a second handle cover.

11. The cutting tool of claim 10, further comprising one or more gripping projections on each of the first handle cover and the second handle cover.

12. The cutting tool of claim 11, wherein the gripping projections are circular in cross section.

13. The cutting tool of claim 11, wherein the gripping projections form a pattern on each of the first and second handle covers.

14. The cutting tool of claim 10, wherein the first handle cover and the second handle cover are disposable.

15. The cutting tool of claim 1, wherein the first section and the second section of the container each comprise a mesh material.

16. The cutting tool of claim 15, wherein the mesh material comprises a metal or a polymer.

17. The cutting tool of claim 1, the first meeting edge comprising a deformable material.

18. The cutting tool of claim 15, the second meeting edge comprising a deformable material.

19. The cutting tool of claim 1, wherein the cutting tool is a medical device.

20. The cutting tool of claim 1, the cutting tool further comprising a hanging hook.

21. A method for removing a foreign object that is embedded in a person or an animal, the method comprising:
    cutting an end of the foreign object off of the foreign object by use of the first and second cutting edges of the cutting tool of claim 1;
    catching or holding the end of the foreign object within the container that is a component of the cutting tool; and
    removing the remainder of the foreign object from a person or an animal.

22. The method of claim 21, wherein the foreign object is a fish hook.

23. The method of claim 21, wherein the foreign object is a piece of jewelry.

24. The method of claim 21, wherein the foreign object is a dental wire or a surgical wire.

25. The method of claim 21, wherein the end of the foreign object extends beyond the container, the foreign object being held between the mating edges of the container.

* * * * *